(12) United States Patent
Sartor et al.

(10) Patent No.: US 8,721,635 B2
(45) Date of Patent: May 13, 2014

(54) BIPOLAR CHONDROPLASTY DEVICE

(75) Inventors: Joe D. Sartor, Longmont, CO (US); Carl W. Almgren, Fort Collins, CO (US)

(73) Assignee: Covidien LP, Mansfield, MA (US)

( * ) Notice: Subject to any disclaimer, the term of this patent is extended or adjusted under 35 U.S.C. 154(b) by 914 days.

(21) Appl. No.: 12/862,914

(22) Filed: Aug. 25, 2010

(65) Prior Publication Data

US 2012/0053579 A1    Mar. 1, 2012

(51) Int. Cl.
*A61B 18/12* (2006.01)
*A61B 18/14* (2006.01)

(52) U.S. Cl.
USPC .................................. 606/34; 606/41; 606/48

(58) Field of Classification Search
USPC ............................. 606/32–35, 41, 48–50, 51; 607/101–105
See application file for complete search history.

(56) References Cited

U.S. PATENT DOCUMENTS

| | | | |
|---|---|---|---|
| 4,955,377 A | 9/1990 | Lennox | |
| 5,683,366 A * | 11/1997 | Eggers et al. | 604/114 |
| 5,743,900 A | 4/1998 | Hara | |
| 5,895,386 A * | 4/1999 | Odell et al. | 606/50 |
| 5,944,715 A * | 8/1999 | Goble et al. | 606/41 |
| 6,090,106 A | 7/2000 | Goble et al. | |
| 6,261,286 B1 | 7/2001 | Goble et al. | |
| 6,293,942 B1 | 9/2001 | Goble et al. | |
| 6,306,134 B1 | 10/2001 | Goble et al. | |
| 6,364,877 B1 | 4/2002 | Goble et al. | |
| 6,409,722 B1 * | 6/2002 | Hoey et al. | 606/34 |
| 6,416,509 B1 | 7/2002 | Goble et al. | |
| 6,780,180 B1 | 8/2004 | Goble et al. | |
| 6,921,399 B2 | 7/2005 | Carmel et al. | |
| 6,953,461 B2 | 10/2005 | McClurken et al. | |
| 7,211,081 B2 * | 5/2007 | Goble | 606/34 |
| 7,549,989 B2 | 6/2009 | Morgan et al. | |
| 7,713,269 B2 | 5/2010 | Auge, II et al. | |
| 2003/0083652 A1 | 5/2003 | Markel | |
| 2005/0059966 A1 | 3/2005 | McClurken et al. | |
| 2006/0116675 A1 | 6/2006 | McClurken et al. | |
| 2007/0016182 A1 | 1/2007 | Lipson et al. | |
| 2008/0197854 A1 | 8/2008 | Valcore et al. | |
| 2009/0275938 A1 | 11/2009 | Roggan | |

FOREIGN PATENT DOCUMENTS

EP          0754437       1/1997
WO    WO 2007113866    10/2007

OTHER PUBLICATIONS

European Search Report for European Application No. 11178796.6 dated Dec. 7, 2011.

* cited by examiner

*Primary Examiner* — Michael Peffley (57) ABSTRACT

A system and method for convectively heating tissue to smooth the surface of the tissue. A fluid, such as saline is distributed across a tissue surface. A bipolar tool is placed within the fluid, but not touching the tissue. An RF signal is sent from a generator through the electrodes to rapidly boil the fluid. Heat is then transferred from the boiling fluid to the tissue resulting in minimal heat damage to tissue. An impedance matching system is used to maximize power received at the bipolar from the generator. Additionally, a control system monitors the boiling fluid to limit arcing.

15 Claims, 6 Drawing Sheets

BIPOLAR CHONDROPLASTY DEVICE

BACKGROUND

1. Technical Field

The present disclosure relates to a system and method for smoothing a tissue surface and, more particularly, for heating the tissue surface convectively via saline using a bipolar tool.

2. Background of Related Art

Chondroplasty refers to surgery of the cartilage. Most commonly, the corrective surgery is performed on the cartilage of the knee.

Chondroplasty is a procedure for encouraging the formation of new scar cartilage or fibrous cartilage in the knee as an aid to healing. Chondroplasty corrects uneven surfaces, tears, loose fragments, or damage from arthritis in a joint. In addition to removing abnormal cartilage and loose fragments in the joint, the main purpose of chondroplasty is to initiate a healing scar tissue response. This improves function of the joint and relieves pain. Although there is no real cure for arthritis, chondroplasty may significantly delay the progression of arthritis. When arthritis or chondral surface injury is present in a knee joint, for example, the white shiny padded Hylan cartilage is injured or partially absent.

One type of chondroplasty is mechanical debridement, which is the process of shaving tissue using a rotary cutter. Mechanical debridement removes large amounts of tissue quickly. However, the shaving leaves a poor finish with up to 0.2 mm of chondrocyte death. Additionally, shaving has poor clinical results that include swelling, pain, and need for recurring surgery.

Another type of chondroplasty is RF debridement. RF debridement removes tissue by rapid ohmic heating of the tissue through an electrical current passing through the tissue from an RF tool contacting the tissue. The ohmic heating causes thermal shrinkage, which results in a smooth surface across the tissue. However, RF debridement may result in chondrocyte death and wound enlargement because of difficulty in thermal margin results.

SUMMARY

In accordance with the present disclosure, a system and method for convectively heating tissue to smooth the surface of the tissue. A fluid, such as saline is distributed across a tissue surface. A bipolar tool is placed within the fluid, but not touching the tissue. An RF signal is sent from a generator through the electrodes to rapidly boil the fluid. Heat is then transferred from the boiling fluid to the tissue resulting in minimal heat damage to tissue. An impedance matching system is used to maximize power received at the bipolar from the generator. Additionally, a control system monitors the boiling fluid to limit arcing.

According to an embodiment of the present disclosure, a method for performing a surgical procedure includes the steps of supplying a fluid across a section of tissue within a patient, and generating a current across electrodes of a bipolar tool to rapidly boil the saline. Further, the method includes the steps of monitoring at least one parameter of the bipolar tool to control the level of boil, and smoothing the section of tissue using heat convectively passed from the bipolar tool through the fluid with neither electrode of the bipolar tool touching any part of the tissue.

According to another embodiment of the present disclosure, a system for performing a surgical procedure includes a fluid distributed across a tissue surface, and a bipolar tool configured with two electrodes. The two electrodes are placed within the fluid and apart from the tissue surface. Further, the system includes a generator configured to supply power to the bipolar tool to generate a current across the electrodes to rapidly boil the fluid and heat from the rapidly boiled fluid smoothes the tissue surface. The system also includes a sensor to measure impedance of the fluid, and a controller configured to determine if fluid is arcing using the measured impedance.

According to another embodiment of the present disclosure, a method for performing a chondroplasty procedure includes the steps of distributing a saline solution across a tissue surface within a patient, and inserting a bipolar tool within the saline without any conductive part of the bipolar tool touching the tissue surface. Further, the method includes the steps of supplying power to the bipolar tool to generate a current across electrodes of the bipolar tool to rapidly boil the saline solution, and sensing an impedance of the saline solution. The method also includes the steps of determining if the saline solution is not boiling, boiling, or arcing using the sensed impedance, and in response to determining the saline solution is boiling, smoothing the tissue surface using heat convectively passed from the bipolar tool through the saline solution.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
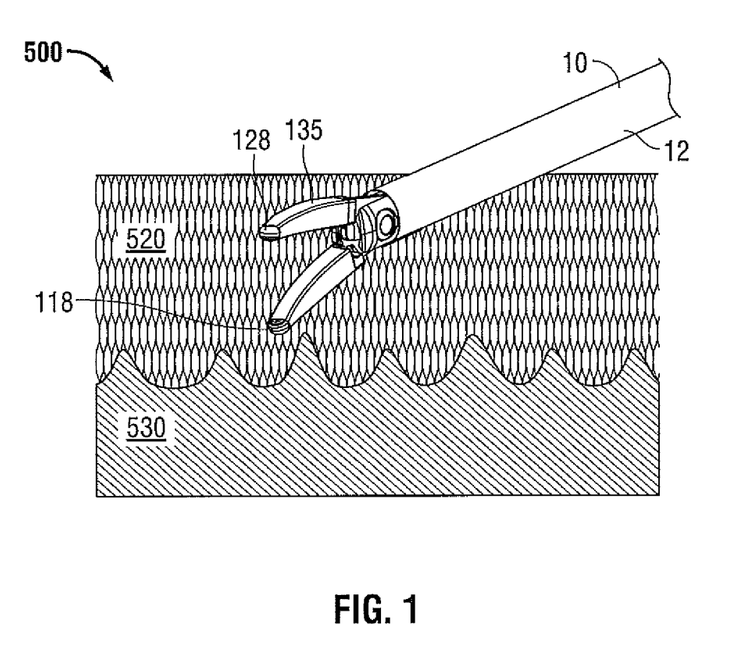
FIG. 1 is a schematic diagram of a chondroplasty system in accordance with an embodiment of the present disclosure.

With reference to FIG. 1, an illustrative embodiment of a chondroplasty system 500 is shown. A fluid 520 is spread across a tissue surface 530. For example, the fluid 520 may be saline with a salt content of about 0.5 to 2.0 percent or any other liquid known in the art. A forcep tool 10 having electrodes 118 and 128 at a distal end thereof is placed within the fluid 520 without touching the tissue 530. As RF energy is supplied from generator 410 (FIG. 2A) current is passed between electrodes 118 and 128 to rapidly boil the fluid 520. Heat from the boiling fluid 520 transfers to the tissue 530 to smooth the surface of the tissue resulting in minimal chondrocyte death. Optimally, the chondrocyte death is about 0.1 mm.

Figure 2A:
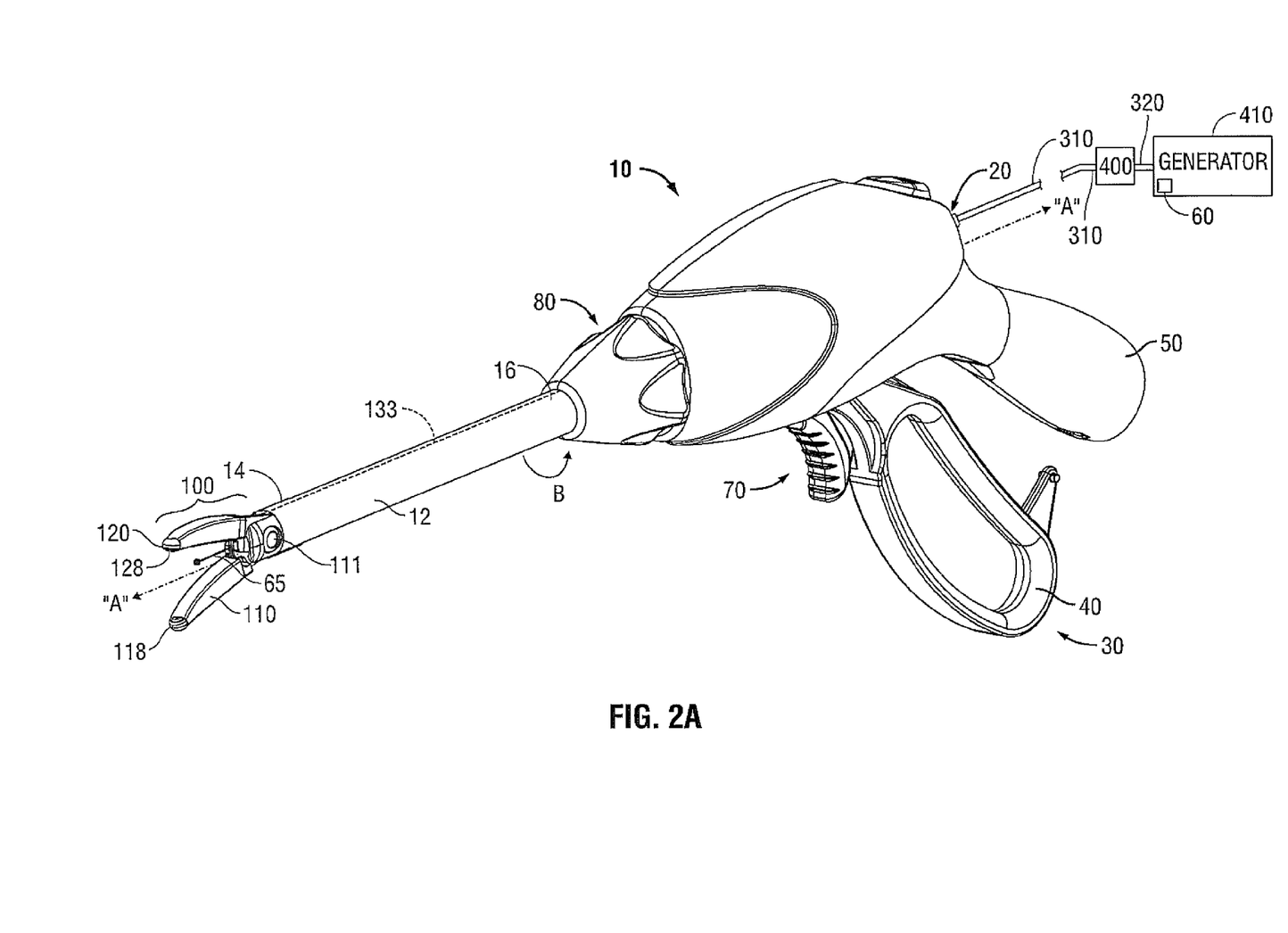
FIG. 2A is a side, perspective view of an endoscopic bipolar forceps showing an end effector assembly including jaw members according to an embodiment of the present disclosure.
Figure 2B:
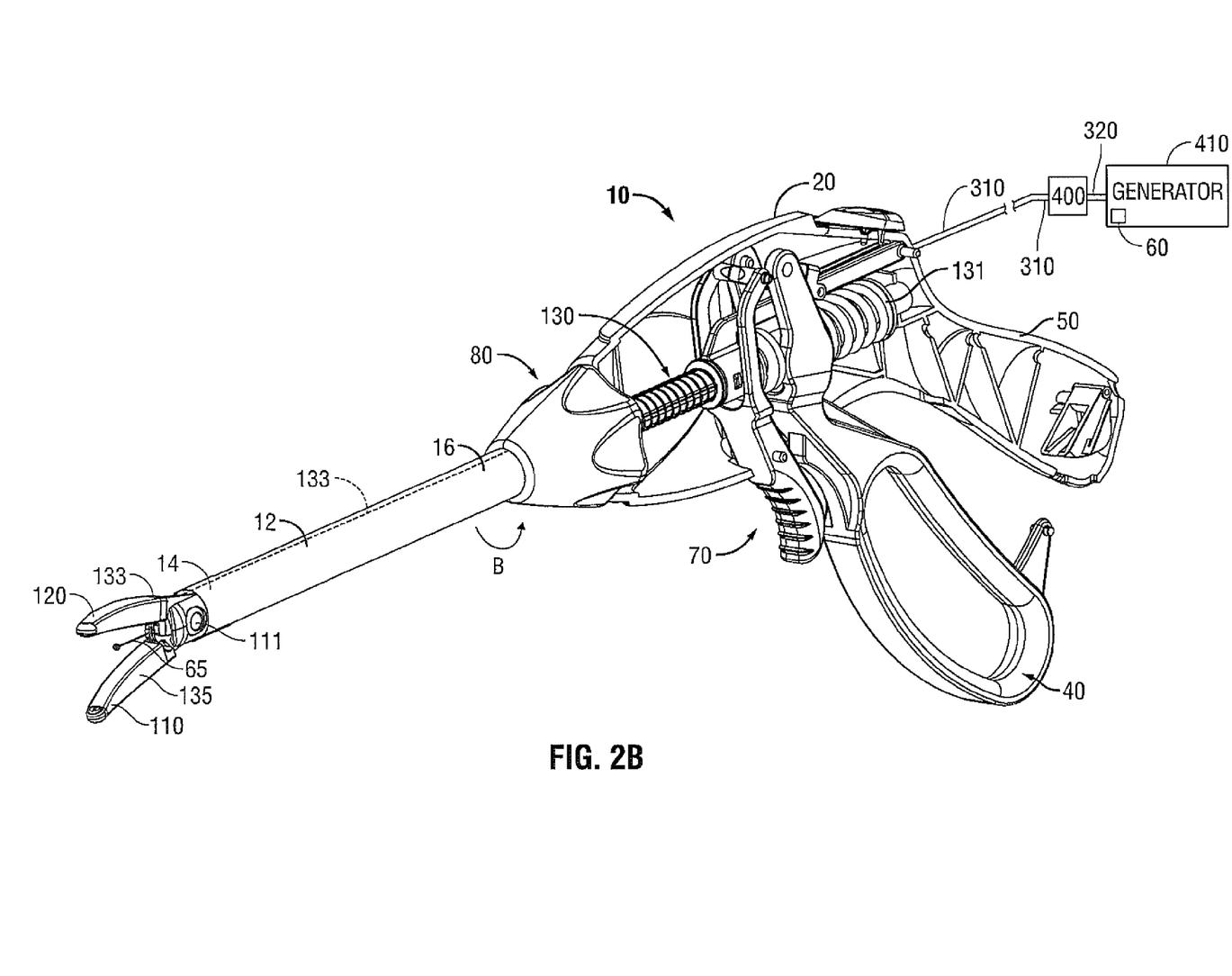
FIG. 2B is a side, perspective view of the endoscopic bipolar forceps depicted in FIG. 2A illustrating internal components associated with a handle assembly of the endoscopic bipolar forceps.

With reference to FIGS. 2A and 2B, an illustrative embodiment of an electrosurgical surgical tool, e.g., a bipolar forceps 10 (forceps 10) is shown. Forceps 10 is operatively and selectively coupled to an electrosurgical generator 410 for performing an electrosurgical procedure. The bipolar forceps 10 may include or be in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., an electrosurgical cable 310) to the forceps 10.

Forceps 10 is shown configured for use with various electrosurgical procedures and generally includes a housing 20, electrosurgical cable 310 that connects the forceps 10 to the electrosurgical generator, a rotating assembly 80 and a trigger assembly 70. For a more detailed description of the rotating assembly 80, trigger assembly 70, and electrosurgical cable 310 (including line-feed configurations and/or connections), reference is made to commonly-owned U.S. patent application Ser. No. 11/595,194 filed on Nov. 9, 2006, now U.S. Patent Publication No. 2007/0173814.

With continued reference to FIGS. 2A and 2B, forceps 10 includes a shaft 12 that has a distal end 14 configured to mechanically engage an end effector assembly 100 operably associated with the forceps 10 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and movable handle 40. In one particular embodiment, fixed handle 50 is integrally associated with housing 20 and handle 40 is movable relative to fixed handle 50 for effecting movement of one or more components, e.g., a drive wire 133, operably associated with a drive assembly 130 (FIG. 2B) via one or more suitable mechanical interfaces, e.g., a linkage interface, gear interface, or combination thereof.

Drive assembly 130 is in operative communication with handle assembly 30 (see FIGS. 2A and 2B) for imparting movement of one or both of a pair of jaw members 110, 120 of end effector assembly 100 to change the distance between electrodes 128, 118. The drive assembly 130 may include a compression spring 131 or a drive wire 133 to facilitate closing the jaw members 110 and 120. Drive wire 133 is configured such that proximal movement thereof causes the movable jaw member, e.g., jaw member 120, and operative components associated therewith, e.g., electrode 128, to pivot inwardly substantially across a length thereof toward the nonmovable jaw member, e.g., jaw member 110. With this purpose in mind, drive rod or wire 133 may be made from any suitable material and is proportioned to translate within the shaft 12. In the illustrated embodiments, drive wire 133 extends through the shaft 12 past the distal end 14, see FIG. 2A for example.

An impedance matching device 400 is connected to the forceps 10 and the generator 410 with cables 310 and 320, respectively. Generally, a generator 410 has an impedance of about 300 ohms, and fluid 520, such as saline has an impedance of about 19 ohms. The impedance of the fluid 520 may change as the fluid is rapidly boiled (See FIG. 4). When the impedance values are not approximately equal, a larger power is required because of losses due to reflection. In one embodiment, the impedance matching device is a transformer with a selected turns ratio, where the transformer is not part of the generator 410 or the forceps 10. For example, the transformer may operate at 472 kHz and have an 18:5 turns ratio. In alternative embodiments, the impedance matching device 400 may be part of the forceps 10 and/or the generator 410.

The end effector assembly 100 further includes a sensor 65 connected to a controller 60 within the generator 410 and/or a controller (not shown) within the forceps 10. The sensor 65 measures the load impedance and/or temperature of the fluid 520. The controller 60 uses the sensed data to adjust power supplied by the generator 410. The power sent by the generator 410 may be increased if the fluid 520 is not boiling or may be decreased if the fluid 520 is arcing. Arcs are short-duration plasmas ignited inside of boiling cavitations.

Figure 3:
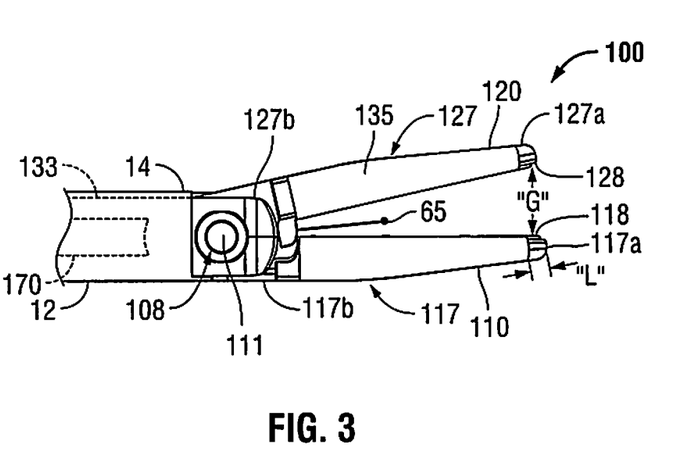
FIG. 3 is a schematic view of the jaw members depicted in FIG. 2A.

Referring now to FIG. 3, end effector assembly 100 is illustrated operably disposed at the distal end 14 of the shaft 12. More particularly, end effector assembly 100 includes opposing jaw members 110 and 120 that are operatively and pivotably coupled to each other and located adjacent the distal end 14 of shaft 12. More particularly, respective proximal ends 117b and 127b of jaw members 110 and 120 are operably secured to the distal end 14 of the shaft 12.

Jaw member 110 includes an electrically conductive electrode 118 that is operably supported on and secured to a distal end 117a of jaw housing 117. Likewise, jaw member 120 includes an electrically conductive electrode 128 that is operably supported on and secured to a distal end 127a of jaw housings 127. Each of the electrodes 118, 128 is formed from a sheet of conductive metal, e.g., surgical steel, of suitable proportion.

Jaw members 110 and 120 are configured to mutually cooperate to adjust the gap distance "G" between electrodes 128, 118. A larger gap distance "G" requires more power and/or time to boil fluid 520 (FIG. 3), such as saline. A smaller gap distance "G" requires less power and/or time to boil the fluid 520, however, a gap distance that is too small may create a short circuit. Jaw members 110, 120 may be stationary or moveable relative to each other. The gap distance "G" may range from about 1.0 mm to 5.0 mm.

The jaw members 110, 120 including jaw housings 127, 117 may be formed from any suitable material, including but not limited to metal, metal alloys, plastic, plastic composites, or combinations thereof.

A non-conductive coating 135, such as a plastic, is applied to jaw members 117, 127 to limit the length "L" of each electrode 118, 128. The length of the electrode can range from about 2.0 mm to 6.0 mm. A larger electrode length "L" will decrease the amount of power and/or time required to boil fluid 520. Accordingly, a smaller electrode "L" will increase the amount of power and/or time required to boil fluid 520.

The jaw members 110 and 120 may be coupled to each other via any suitable coupling methods. In the illustrated embodiment, an opening 108 is defined in and extends through the each of the jaw housings 117 and 127 and is configured to receive a pivot pin 111. Opening 108 is shown engaged with pivot pin 111 and as such is not explicitly visible.

Figure 4:
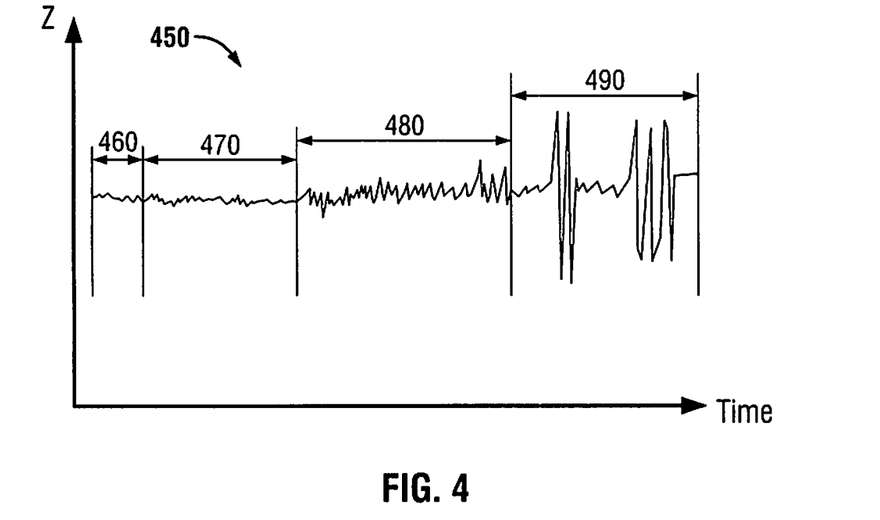
FIG. 4 is a graph depicting the variation in impedance of the fluid during different phases in accordance with an embodiment of the present disclosure.

FIG. 4 is a graph 450 depicting the variation in impedance of the fluid 520 during different boiling phases. The impedance is measured by sensor 65 and sent to controller 60. During a first phase 460, there is zero variation in impedance as measured by sensor 65, and therefore there is no boiling. If the first phase lasts for an extended period of time, then the controller may decide to increase the power supplied by the generator. During a second phase 470, there is a low amount of variation in impedance signifying that the fluid 520 is gently boiling. Similar to the first phase 460, the controller may increase the power if the second phase 470 lasts for an extended period of time. During a third phase 480, there is a medium amount of variation in impedance signifying that the fluid is violently boiling. The third phase 480 allows for the fluid to rapidly boil with minimal arcing, which is the optimum phase to perform chondroplasty using chondroplasty system 500. During the fourth phase 490, there is a high amount of variation in impedance signifying arcing. In response to the sensor 65 reading a high amount of variation, the controller 60 would turn off or reduce the amount of power supplied by the generator 410.

Figure 5:
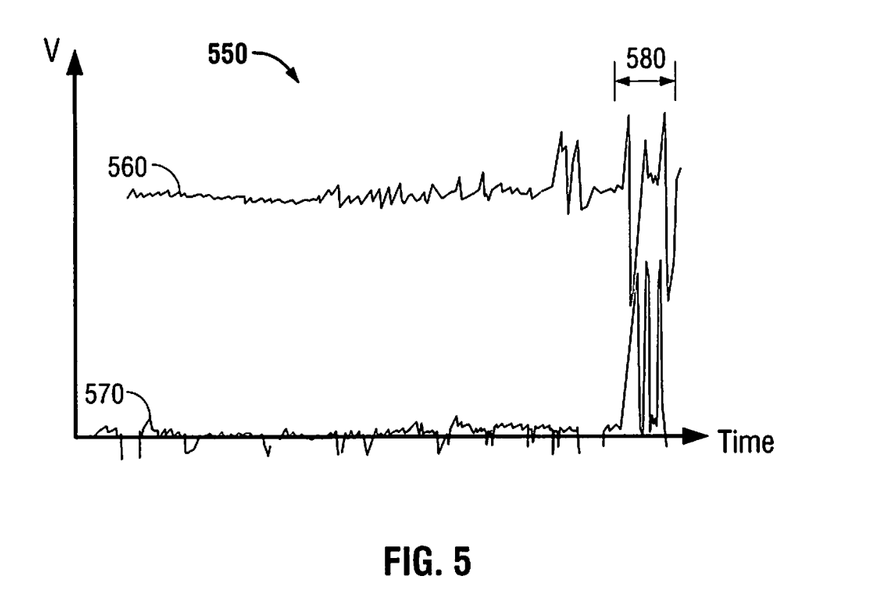
FIG. 5 is a graph of an arc detection system in accordance with an embodiment of the present disclosure.

FIG. 5 is a graph 550 of an arc detection system using a harmonic signal 570. The sensor 65 measures the impedance of the fluid 520 which is shown over time as line 560. The controller 60 compares the measured impedance 560 to a harmonic waveform 570. Region 580 of the graph 550 shows arcing when the harmonic waveform 570 overlaps with measured impedance. The harmonic waveform 570 may be between any integer multiple of the fundamental frequency, greater than one. In one embodiment, the harmonic waveform 570 is a fourth harmonic voltage and the fundamental frequency is 472 kHz.

Figure 6:
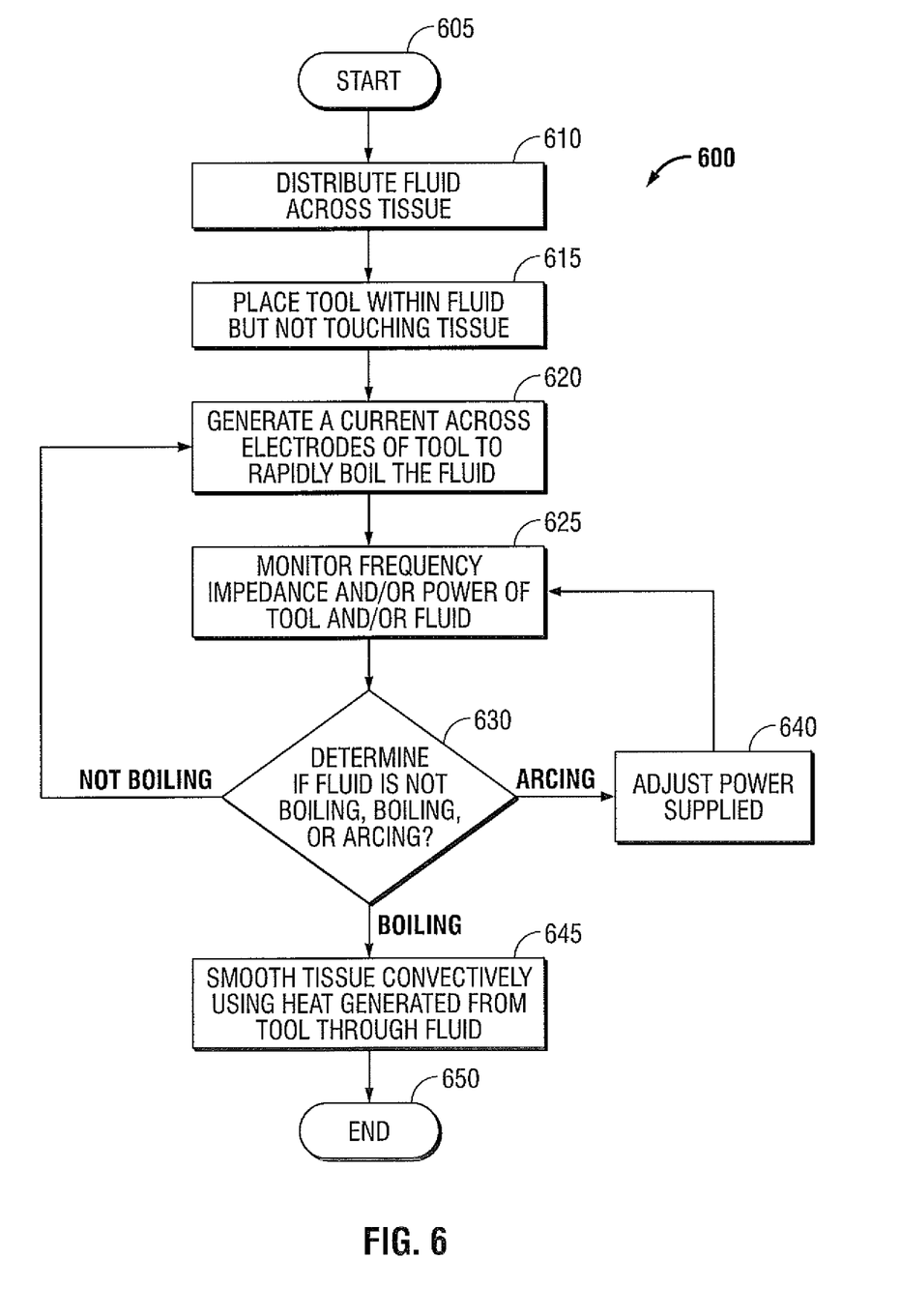
FIG. 6 is a flow diagram of a process for performing a chondroplasty surgical procedure in accordance with an embodiment of the present disclosure.

FIG. 6 is a flow diagram of process 600 for a chondroplasty surgical procedure according to an embodiment of the invention. After the process 600 starts at step 605, fluid 520, such as saline, is distributed across the tissue 530 at step 610. Next, the tool 10 is placed within the fluid 520 at step 615. The tool 10 is placed, such that no part of the tool 10 is touching the tissue 530. The generator 410 supplies power to tool 10 to generate a current across electrodes 128, 118 to rapidly boil the fluid 520 at step 620. Then, the controller 60 monitors the frequency, impedance, and/or power of the tool 10 and/or fluid 520 using sensor 65 in step 625. The controller 60 determines if the fluid 520 is not boiling, boiling, or arcing at step 630. This determination can be based on impedance measurements and/or using a harmonic waveform 570 such as the fourth harmonic waveform. If the fluid is not boiling, then the generator 410 continues to generate a current across the electrodes 128, 118 at step 620. The generator 410 may increase the power supplied to the electrodes 128, 118 if necessary. If the fluid is arcing, then the power sent from the generator 410 is reduced at step 640. If the fluid is boiling, then the tissue 530 is smoothed convectively using heat generated from the tool 10 through the fluid 520 at step 645, and then the process 600 ends at step 650.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for performing a surgical procedure, comprising:
   distributing a fluid across a section of tissue within a patient;
   generating a current across electrodes of a bipolar tool to rapidly boil the fluid;
   monitoring impedance of the bipolar tool to control the level of boil;
   generating a harmonic waveform;
   comparing the harmonic waveform with a monitored impedance to determine if the harmonic waveform overlays the monitored impedance;
   in response to determining the harmonic waveform overlaps the monitored impedance, reducing the power supplied by a generator; and
   smoothing the section of tissue using heat convectively passed from the bipolar tool through the fluid with neither electrode of the bipolar tool touching any part of the tissue.

2. The method according to claim 1, further comprising:
   determining an amount of variation in impedance; and
   in response to determining a high amount of variation in impedance, reducing the power supplied by the generator to reduce arcing.

3. The method according to claim 1, wherein the harmonic waveform is a fourth harmonic waveform.

4. The method according to claim 1, wherein the fluid is saline with a salt concentration between about 0.5 to 2.0 percent.

5. A system for performing a surgical procedure, comprising:
   a fluid adapted to be distributed across a tissue surface;
   a bipolar tool configured with two electrodes, wherein the two electrodes are placed within the fluid and apart from the tissue surface;
   a generator configured to supply power to the bipolar tool to generate a current across the electrodes to rapidly boil the fluid and heat from the rapidly boiled fluid smoothes the tissue surface;
   a sensor to measure impedance of the fluid; and
   a controller configured to determine if fluid is arcing using a measured impedance;
   wherein the controller is configured with a harmonic waveform and determines that the fluid is arcing when the measured impedance and the harmonic waveform overlap.

6. The system according to claim 5, further comprising:
   an impedance matching device configured between the generator and the bipolar tool to substantially match an impedance of the fluid with an impedance of the generator.

7. The system according to claim 5, wherein each electrode is coated with a non-conductive coating to limit the size of the electrode.

8. The system according to claim 7, wherein the size of each electrode is between about 2.0 mm and 6.0 mm.

9. The system according to claim 5, wherein the controller is configured to determine the fluid is arcing when a high amount of variation in impedance is sensed.

10. A method for performing a chondroplasty procedure, comprising:
    distributing a saline solution across a tissue surface within a patient;
    inserting a bipolar tool within the saline solution without an conductive part of the bipolar tool touching the tissue surface;
    supplying power to the bipolar tool to generate a current across electrodes of the bipolar tool to rapidly boil the saline solution;
    sensing an impedance of the saline solution;
    generating a fourth harmonic waveform;
    comparing the fourth harmonic waveform with a sensed impedance of the saline solution;
    determining the saline solution is arcing based on a high amount of variation of the sensed impedance and overlap between the fourth harmonic waveform and the sensed impedance of the saline solution;
in response to determining the saline solution is arcing, reducing the power supplied to the bipolar tool;
determining if the saline solution is not boiling, or arcing using the sensed impedance; and
in response to determining the saline solution is boiling, smoothing the tissue surface using heat convectively passed from the bipolar tool through the saline solution.

11. The method according to claim 10, further comprising:
determining the saline solution is not boiling based on zero to low amount of variation of impedance sensed; and
in response to determining the saline solution is not boiling, increasing the power supplied to the bipolar tool.

12. The method according to claim 10, wherein the generated heat from the electrodes via the saline solution shrinks the tissue to create a smooth surface and minimal chondrocyte death.

13. The method according to claim 10, wherein the tissue is cartilage of the patient's knee.

14. A method for performing a surgical procedure, comprising:
distributing a fluid across a section of tissue within a patient;
generating a current across electrodes of a bipolar tool to rapidly boil the fluid;
monitoring at least one parameter of the bipolar tool to control the level of boil;
decreasing a gap distance between the electrodes of the bipolar tool to decrease time or power required to rapidly boil the fluid, wherein the gap distance between the electrodes ranges from about 1.0 mm to 5.0 mm; and
smoothing the section of tissue using heat convectively passed from the bipolar tool through the fluid with neither of the electrodes of the bipolar tool touching any part of the tissue.

15. A method for performing a chondroplasty procedure, comprising:
distributing a saline solution across a tissue surface within a patient;
inserting a bipolar tool within the saline solution without any conductive part of the bipolar tool touching the tissue surface;
supplying power to the bipolar tool to generate a current across electrodes of the bipolar tool to rapidly boil the saline solution;
sensing an impedance of the saline solution;
determining if the saline solution is not boiling or arcing using a sensed impedance;
adjusting a gap distance to adjust the amount of time for the saline solution to rapidly boil; and
in response to determining the saline solution is boiling, smoothing the tissue surface using heat convectively passed from the bipolar tool through the saline solution.

* * * * *